US009090893B2

(12) United States Patent
Papes et al.

(10) Patent No.: US 9,090,893 B2
(45) Date of Patent: *Jul. 28, 2015

(54) CONSTITUTIVE PROMOTERS FROM POPLAR AND USES THEREOF

(71) Applicant: FIBRIA CELULOSE S.A., São Paulo (BR)

(72) Inventors: Fabio Papes, Campinas/SP (BR); Paulo Arruda, Campinas/SP (BR)

(73) Assignee: FIBRIA CELULOSE S.A., Sao Paulo (BR)

( * ) Notice: Subject to any disclaimer, the term of this patent is extended or adjusted under 35 U.S.C. 154(b) by 85 days.

This patent is subject to a terminal disclaimer.

(21) Appl. No.: 13/713,694

(22) Filed: Dec. 13, 2012

(65) Prior Publication Data
US 2013/0133113 A1   May 23, 2013

Related U.S. Application Data

(60) Continuation of application No. 13/150,611, filed on Jun. 1, 2011, now Pat. No. 8,420,796, which is a division of application No. 11/917,765, filed as application No. PCT/BR2006/000139 on Jul. 7, 2006, now Pat. No. 7,956,174.

(60) Provisional application No. 60/697,628, filed on Jul. 8, 2005.

(51) Int. Cl.
*C12N 15/82*   (2006.01)
*C12N 15/10*   (2006.01)
*A01H 5/00*   (2006.01)
*C12N 15/11*   (2006.01)

(52) U.S. Cl.
CPC ............ *C12N 15/11* (2013.01); *C12N 15/8216* (2013.01)

(58) Field of Classification Search
CPC .... C12N 15/8216; C12N 15/11; C12N 15/82; C12N 15/00; C12N 15/63
See application file for complete search history.

(56) References Cited

U.S. PATENT DOCUMENTS

| 6,528,701 | B1 | 3/2003 | Wang et al. |
| 7,288,696 | B2 | 10/2007 | Chiang et al. |
| 2004/0088760 | A1 | 5/2004 | Allen et al. |

FOREIGN PATENT DOCUMENTS

WO   WO-2004/104174 A2   12/2004

OTHER PUBLICATIONS

A. de la Pena et al., "Transgenic rye plants obtained by injecting DNA into young floral tillers", Nature, vol. 325, Jan. 15, 1987, pp. 274-276.
A. Depicker et al., "Nopaline Synthase: Transcript Mapping and DNA Sequence", Journal of Molecular and Applied Genetics, 561-573, 1982.
Carol A. Rhodes et al., "Genetically Transformed Maize Plants from Protoplasts", Science, vol. 240, Apr. 8, 1988, pp. 204-207.
Database Genbank [Online] *Populus nigra* PnUB1 mRNA Jun. 30, 2004, T. Igasaki: XP002526731.
Database Genbank [Online] *Populus ubiquitin* mRNA May 17, 2000, Degueret et al.: XP002526729.
Database UniProt [Online] Polyubiquitin *Populus nigra*, Jul. 19, 2004, T. Igasaki: XP002526730.
Database UniProt [Online] Polyubiquitin Populus. Oct. 1, 2000, Degueret et al.: XP002526728.
David Clapham et al., "Enhancement of short- and medium-term expression of transgenes in embryogenic suspensions of *Picea abies* (L.) Karst", Journal of Experimental Botany, vol. 46, No. 287, pp. 655-662, Jun. 1995.
David Gordon et al., "Consed: A Graphical Tool for Sequence Finishing", Genome Research, Jan. 25, 2008, pp. 195-202.
David M. Stalker et al., "Herbicide Resistance in Transgenic Plants Expressing a Bacterial Detoxification Gene", Science, vol. 242, Oct. 21, 1988, pp. 419-423.
Dilip M. Shah et al., "Engineering Herbicide Tolerance in Transgenic Plants", Science, vol. 233, Jul. 25, 1986, pp. 478-481.
F. Guerineau et al., "Sulfonamide resistance gene for plant transformation", Plant Molecular Biology 15: 127-136, 1990.
Final Office Action U.S. Appl. No. 11/917,765 dated Aug. 9, 2010.
Hairong Wei et al., "Comparative expression analysis of two sugarcane polyubiquitin promoters and flanking sequences in transgenic plants", J. Plant Physiol. 160, 1241-1251 (2003).
Horst Lorz et al., "Gene transfer to cereal cells mediated by protoplast transformation", Mol. Gen. Genet. (1985) 199: 178-182.
J. Gielen et al., "The complete nucleotide sequence of the TL-DNA of the *Agrobacterium tumefaciens* plasmid pTiAch5", The EMBO Journal, vol. 3, No. 4, pp. 835-846, 1984.
J. Wang et al., "Structure, expression and promoter activity of two polyubiquitin genes from rice (*Oryza sativa* L.)", Plant Science vol. 156, No. 2, Jul. 28, 2000, pp. 201-211.
Jane Aldrich et al., "RAPD Analysis in Flax: Optimization of Yield and Reproducibility using KlenTaq 1DNA Polymerase, Chelex 100, and Gel Purification of Genomic DNA", Plant Molecular Biology Reported, vol. 11(2)1983, pp. 128-141.
Joan E. Garbarino et al., "Isolation of a Polyubiquitin Promoter and Its Expression in Transgenic Potato Plants", Plant Physiol. (1995) 109:1371-1378.

(Continued)

*Primary Examiner* — Brent T Page
(74) *Attorney, Agent, or Firm* — Arent Fox LLP

(57) ABSTRACT

The present invention relates to nucleic acid molecules corresponding to regulatory portions of genes whose expression is constitutive. The invention also relates to compositions and methods of using the same to regulate the expression, in a constitutive manner, of genes and/or any kind of nucleotide sequences in a plant. Nucleic acid molecules and its compositions include novel nucleotide sequences for constitutive promoter identified in and isolated from poplar (*Populus* spp). Methods for expressing genes and/or any kind of nucleotide sequences in a plant using the promoter sequences disclosed herein are provided. The methods comprise stably incorporating into the genome of a plant cell a nucleotide sequence operably linked to one or more of the constitutive promoters of the present invention and regenerating a stably transformed plant that expresses the nucleotide sequence.

25 Claims, 6 Drawing Sheets

(56) References Cited

OTHER PUBLICATIONS

Ko Shimamoto et al., "Fertile transgenic rice plants regenerated from transformed protoplasts", Nature, vol. 338, Mar. 16, 1989, 274-276.

Leandrop Pena et al., "Early Events in Agrobacterium-mediated Genetic Transformation of Citrus Expants", Annals of Botany 94: 67-74, 2004.

M. D. Matteucci et al., "Synthesis of Deoxyoligonucleotides on a Polymer Support", J. Am. Chem. Soc. 1981, 103, 3185-3191.

M. De Block et al., "Engineering herbicide resistance in plants by expression of a detoxifying enzyme", The EMBO Journal, vol. 6, No. 9, pp. 2513-2518, 1987.

Michael Bevan, "Binary Agrobacterium vectors for plant transformation", Nucleic Acid Research, vol. 12, No. 22, 1984, pp. 8711-8721.

Nicole Bechtold et al., "In planta Agrobacterium mediated gene transfer by infiltration of adult *Arabidopsis thaliana* plants", Life sciences 1993: 316; 1194-1199.

Non-Final Office Action U.S. Appl. No. 11/917,765 dated Mar. 5, 2010.

Non-Final Office Action U.S. Appl. No. 11/917,765 dated Oct. 27, 2009.

Notice of Allowance U.S. Appl. No. 11/917,765 dated Feb. 3, 2011.

P. Genschik et al., "Structure and promoter activity of a stress and developmentally regulated polyubiquitin-encoding gene of *Nicotiana tabacum*", Gene 148 (1994) pp. 195-202.

Petra Kawalleck et al., "Polyubiquitin gene expression and structural properties of the ubi4-2 gene in *Petroselinum crispum*", Plant Molecular Biology 21: 673-684, 1993.

R. Nagel et al., "Electroporation of binary Ti plasmid vector into *Agrobacterium tumefaciens* and *Agrobacterium rhizogenens*", FEMS Microbiology Letters 67 (1990) 325-328.

R.B. Horsch et al., "A Simple and General Method for Transferring Genes into Plants", Science, vol. 227, 1229-1231.

Robert T. Fraley et al., "Expression of bacterial genes in plant cells", Proc. Natl. Acad. Sci. USA, vol. 80, pp. 4803-4807, Aug. 1983.

S.L. Beaucage et al., "Deoxynucleside Phosphoramidites—A New Class of Key Intermediates for Deoxypolynucleotide Synthesis", Tetrahedron Letters, vol. 22, No. 20, pp. 1859-1862, 1981.

Stephen F. Altschul et al., "Gapped BLAST and PSI-BLAST: a new generation of protein database search programs", Nucleic Acids Research, 1997, vol. 25, No. 17, pp. 3389-3402.

Supplementary European Search Report EP 06 75 2719 dated May 8, 2009.

T.M. Klein et al., "High-velocity microprojectiles for delivering nucleic acids into living cells", Nature, vol. 327, May 7, 1987, pp. 70-73.

Xiaoqiu Huang et al., "CAP3: A DNA Sequence Assembly Program", Genome Research, 1999, pp. 868-877.

A

PdUBQ:GUS

B

35S:GUS

CONSTITUTIVE PROMOTERS FROM POPLAR AND USES THEREOF

RELATED APPLICATION

This application is a continuation of U.S. application Ser. No. 13/150,611, filed Jun. 1, 2011; which is a divisional of U.S. application Ser. No. 11/917,765, filed Jan. 24, 2008, and issued as U.S. Pat. No. 7,956,174; which is the U.S. national stage of PCT/BR2006/000139, filed Jul. 7, 2006; and claims priority to U.S. Provisional Application No. 60/697,628, filed Jul. 8, 2005. The disclosure of each application is incorporated by reference it its entirety.

FIELD OF THE INVENTION

The invention relates generally to the field of molecular biology, biochemistry and agriculture. More particularly, the invention relates to polynucleotides suitable for regulating gene expression in plants and generation of improved transgenic plants.

BACKGROUND AND PRIOR ART OF THE INVENTION

Modification of a plant trait through genetic engineering depends upon the insertion into the plant genome of a polynucleotide construct containing the gene of interest, operably linked to a promoter that is functional in the transgenic plant. Within a plant genome, any single gene is, in general, operably linked to a promoter that will determine when and where, within the plant tissues and organs, the gene should be expressed. Sometimes, it is of interest to use a promoter capable of directing the expression of the operably linked gene to most tissues of the plant. These promoters are known in the art as constitutive promoters. To be most useful, a constitutive promoter should be able to direct the expression to all cells, tissues and organs of the plant. Constitutive promoters should also preferably be able to determine the expression of the operably linked gene to the same high level in all tissues and organs, throughout the plant's life cycle. Therefore if one wants to express a gene of interest in several or all tissues or organs within a transgenic plant, constitutive promoters must be used.

In a number of situations the expression of particular genes in most or all tissues or organs confers a phenotype of interest to the plant. For example, if one wants to improve the plant's disease resistance, a gene that confers such phenotype linked to a constitutive promoter is inserted, rather than using tissue-specific promoters that would allow the gene to be expressed in selected plant tissues, causing in some cases undesirable phenotypes.

Thus far, the production of genetically engineered plants expressing useful and/or desirable traits requires the availability of promoters that permit the gene or genes of interest to be expressed constitutively. Thus, isolation and characterization of constitutive promoters that can serve as regulatory regions for expression of heterologous nucleotide sequences of interest in most or all tissues and organs is essential for the genetic engineering of plants.

SUMMARY OF THE INVENTION

The present invention relates to isolated regulatory nucleic acid molecules, initially isolated from the genome of *Populus* sp, and methods for regulating expression of heterologous nucleotide sequences. It is an object of the invention to provide isolated nucleic acid molecules which function as promoters that are able to direct constitutive expression of genes of interest. The regulatory nucleic acid molecules of the present invention correspond to promoter sequences of several different polyubiquitin genes, which are expressed at high and constitutive levels in tissues of *Populus* sp. When these promoters are associated in a transgenic plant with a gene, such as a heterologous gene, the gene in question is expressed at high levels in most if not all tissues of said transgenic plant. Methods of using the constitutive promoters disclosed herein, for regulating expression of heterologous nucleotide sequences in a constitutive manner in a plant, are provided.

The promoters of the invention were identified through the analysis of a collection of Expressed Sequence Tags (ESTs) from *Populus* sp, representing apical shoot, bark, cambium, seed, xylem, leaf and root tissues. Based on the expression profile of those ESTs among the different tissues, three polyubiquitin genes were shown to be highly and constitutively expressed in several tissues of *Populus*. The promoters of these three genes are referred to hereinafter as PdUBQ1, PdUBQ2, and PdUBQ3, respectively.

The PdUBQ promoters of the invention are set forth at SEQ ID NOs.: 1, 2 and 3. Fragments of these nucleotide sequences, comprising at least 30 consecutive nucleotides, are also a feature of this invention. These fragments, while not necessarily representing promoters or sequences with promoter activity, function as antisense molecules and disable naturally-occurring expressed genes. The invention further comprises nucleotide sequences having at least 65% identity to the sequences set forth in SEQ ID NOs.: 1, 2 and 3 or to fragments thereof, and nucleotide sequences that hybridize under high stringency conditions to any one of the aforementioned sequences, i.e., SEQ ID NOS: 1, 2, and 3.

"Stringent conditions" as used herein, refers to parameters with which the art is familiar, such as hybridization in 3.5× SSC, 1×Denhardt's solution, 25 mM sodium phosphate buffer (pH 7.0), 0.5% SDS, and 2 mM EDTA for 18 hours at 65° C., followed by 4 washes of the filter at 65° C. for 20 minutes, in 2×SSC, 0.1% SDS, and a final wash for up to 20 minutes in 0.5×SSC, 0.1% SDS, or 0.3×SSC and 0.1% SDS for greater stringency, and 0.1×SSC, 0.1% SDS for even greater stringency. Other conditions may be substituted, as long as the degree of stringency is equal to that provided herein, using a 0.5×SSC final wash.

Other facets of the present invention include constructs, such as expression vectors, comprising any one of the promoters disclosed herein operably linked to a nucleotide sequence of interest, which may encode a desired protein. The PdUBQ promoters disclosed herein are capable of driving expression of polynucleotides of interest in a plant cell and said promoters comprise any one of the nucleotide sequences of the present invention.

Also as part of the invention are recombinant plants or plant cells having stably incorporated into their genomes any one of the constructs described above or one or more of the promoters per se.

Methods of the invention also include methods for stably incorporating the molecules of the invention into cells.

DETAILED DESCRIPTION OF PREFERRED EMBODIMENTS

One feature of the present invention comprises isolated nucleotide sequences for plant promoters, particularly the three constitutive promoters set forth in SEQ ID NOs.: 1, 2 and 3. These promoters were isolated from the 5' untranslated region flanking the transcription initiation sites of polyubiquitin genes. Methods for the isolation of the promoters are well known in the art and include bioinformatics tools for gene assembly such as Phred, Phrap, Consed (Gordon et al. (1998) *Genome Research.* 8:195-202), sequence alignment (Durbin et al. (1998) *Biological sequence analysis—probabilistic models of proteins and nucleic acids*. Cambridge University Press, Cambridge, UK), functional search (Altschul et al. (1997) *Nucleic Acid Res.* 25:3389-3402) and PCR techniques (Sambrook and Russell (2001) *Molecular Cloning—a laboratory manual*. Cold Spring Harbor Laboratory Press, Cold Spring Harbor, N.Y., USA). Some of these methods are described in Example 1 infra, and all are incorporated by reference.

The disclosed nucleic acid molecules in one aspect span 2.7 kb starting at the ATG start codon for the coding region of the polyubiquitin genes in question. The isolated nucleic acid molecules are referred to herein as promoters. Promoters correspond to the nucleic acid molecules whose function is to regulate the expression of a gene. A promoter generally comprises specific signaling sequences called boxes, arranged along the promoter sequence, such that its composition determines the temporal and spatial expression of a gene that is under its regulatory control. "Promoter" or "transcriptional initiation region" means a regulatory region of DNA usually comprising a TATA box capable of directing RNA polymerase II to initiate RNA synthesis at the appropriate transcription initiation site for a particular coding sequence. A promoter may additionally comprise other recognition sequences, generally positioned upstream, or 5', to the TATA box, referred to as upstream promoter elements, which influence the transcription initiation rate. It is recognized that, having identified the nucleotide sequences for the promoter regions disclosed herein, it is within the state of the art to isolate and to identify additional regulatory elements in the 5' untranslated region upstream from the particular promoter regions identified herein.

Thus the promoter regions disclosed herein are generally further defined by additional upstream regulatory elements such as those responsible for tissue and temporal expression of the coding sequence, enhancers and the like. In the same manner, the promoter elements, which enable expression of the downstream gene in most or all tissues, can be identified, isolated and used with other core promoters to confer constitutive expression.

As part of the present invention, three promoters that direct the expression of genes in most or all tissues were identified and isolated from *Populus* sp.

Figure 1:
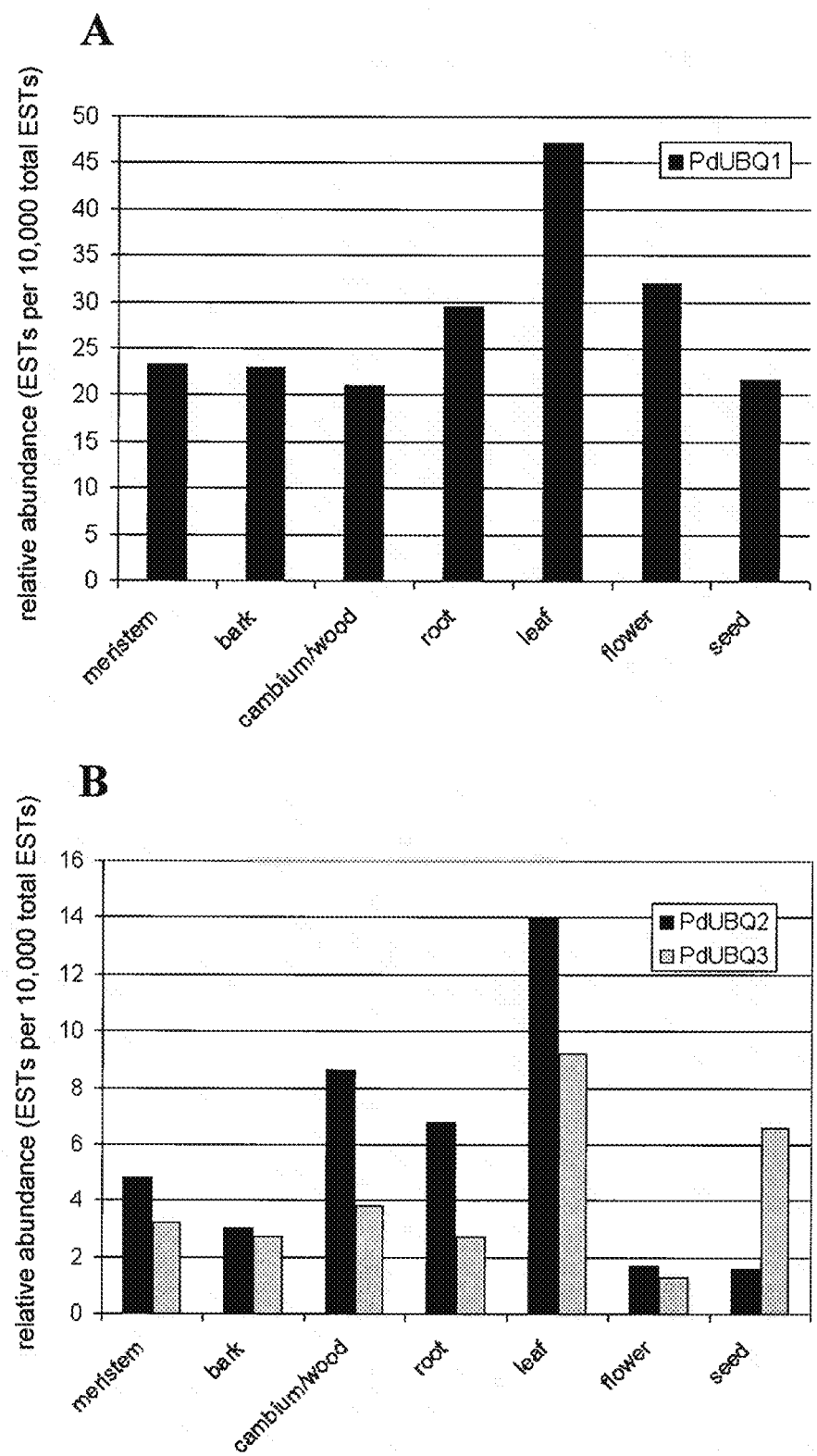
FIG. 1A shows the expression profile in a set of *Populus* tissues of the polyubiquitin gene which is under the control of the promoter PdUBQ1 of the invention.
FIG. 1B shows the expression profile in a set of *Populus* tissues of the polyubiquitin genes which are under the control of the promoters PdUBQ2 and PdUBQ3 of the invention.

The native polyubiquitin genes from *Populus* sp. encode isoforms of hexameric polyubiquitin, a protein involved in the controlled degradation of cellular proteins. The polyubiquitin genes whose promoters are disclosed herein are expressed at high levels in most tissues of *Populus* sp (FIG. 1).

The constitutive promoter sequences of the present invention drive the expression of operably linked nucleotide sequences in a constitutive manner. Thus, the constitutive promoter sequences disclosed herein can be used to express an operably linked sequence of interest in most tissues of a plant. Since the promoter sequences disclosed herein were isolated from a dicot species, they are useful in directing the constitutive expression of operably linked genes when transformed in dicot species, although their uses in monocots and gymnosperms are also contemplated, as are the resulting recombinant plants and plant parts.

In addition, the promoters of the invention can be used to inhibit the expression of genes when used in constructs together with DNA fragments from a gene of interest in the antisense orientation or in a configuration that promotes hairpin post-transcriptional gene silencing, as is known to one of skill in the art.

"Variants" is intended to include substantially similar sequences. Naturally and non-naturally occurring "variants" of PdUBQ promoter sequences within the invention are nucleic acid molecules having at least 65% sequence identity with one of the promoter sequences disclosed herein, SEQ ID NO: 1, SEQ ID NO: 2 or SEQ ID NO: 3. "Variants" also include nucleic acids molecules that hybridize under stringent conditions, as defined herein, to the nucleic acid molecules of SEQ ID NO.: 1, SEQ ID NO.: 2 or SEQ ID NO.: 3 or the complement of the sequences of SEQ ID NO.: 1, SEQ ID NO.: 2 or SEQ ID NO.: 3. Alternatively, such nucleic acids are those having a nucleotide sequence that is the complement of one of the full-length sequences of SEQ ID NOs.: 1, 2 or 3, or portions thereof. Other variants of the promoter sequences of the invention are polynucleotides that share at least 65% sequence identity, preferably at least 80%, more preferably at least 90%, and most preferably at least 95%, to the sequences of SEQ ID NO: 1, 2 or 3 or to the complement of the sequences of SEQ ID NOs: 1, 2 or 3.

"Stringent conditions", as used herein, refers to the parameters set forth supra.

For purposes of the present invention, sequence identity to any of the promoter sequences disclosed herein may be determined, e.g., using known methodologies such as the BLAST program, or any sequence alignment program that allows the alignment of identical nucleotides and verification of mismatches between non-identical nucleotides so that the percentage of identity of compared sequences can be estimated.

The promoters of the invention may be used to express a gene of interest. For example, by using any one of the promoters of the invention, the expression of native and/or non-native genes can be accomplished in desired tissues of a plant.

The native and/or non-native genes include those encoding enzymes, transporters, cofactors, transcription factors and a number of other genes that would affect a desirable trait in plants.

For the present invention, it is recognized that any gene of interest can be operably linked to any one of the promoters of the invention and expressed in a plant.

The promoters of the present invention, when operably linked to a gene of interest and stably incorporated into a plant genome, drive expression of said gene of interest in all plant tissues, at high levels. It is to be recognized, of course, that the promoters disclosed herein may drive the expression of genes in some tissues more prominently than to others.

Figure 3:
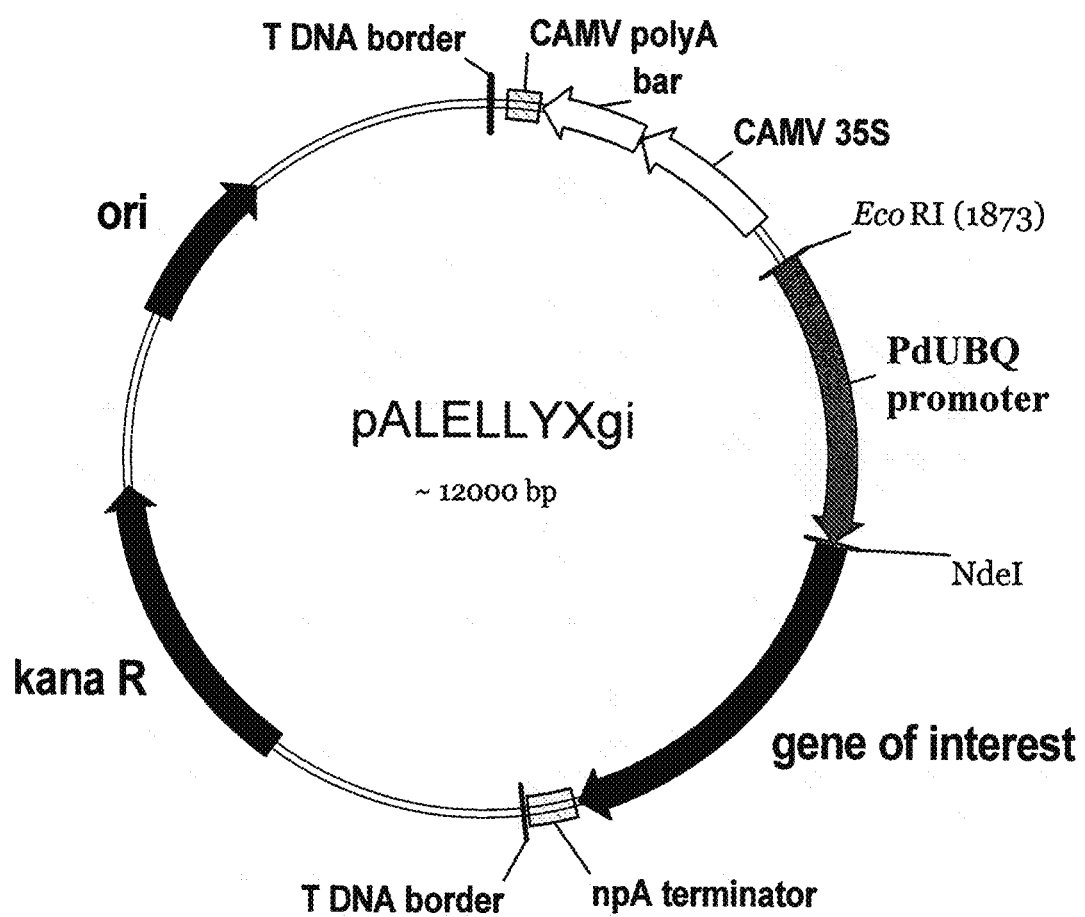
FIG. 3 schematically illustrates a generic plant expression vector which delineates the various parts of the vector. Variations are described in the specification.

Constructs containing a promoter of the present invention and an operably linked gene of interest may be provided in expression cassettes or vectors, as depicted in FIG. 3. Such expression cassettes or vectors comprise one of the promoters of the present invention, operably linked to a gene of interest. Such an expression cassette or vector may contain, e.g., restriction sites for insertion of the gene of interest under the transcriptional control of the constitutive PdUBQ promoter. The expression cassette or vector may additionally contain a number of other nucleotide sequences, including selectable marker genes, transcriptional and translational initiation sequences, and plant transcriptional and translational termination sequences. The termination region may be from the same group as the DNA sequence of interest or may be from the Ti-plasmid of *A. tumefaciens*, such as the octopine synthase and nopaline synthase termination regions (Gielen et al., EMBO J., 3:835-846 (1984), Depicker et al., Mol. and Appl. Genet., 1:561-573 (1982)). Other termination rights may be used as well.

Reporter genes or selectable marker genes may be included in the expression systems. Examples of suitable reporter genes known in the art can be found in, for example, Jefferson et al. (1991) in *Plant Molecular Biology Manual*, ed. Gelvin et al. (Kluwer Academic Publishers), pp. 1-33. Selectable marker genes for selection of transformed cells or tissues can include genes that confer herbicide resistance. Examples of suitable selectable marker genes include, but are not limited to, genes encoding resistance to sulfonamide (Guerineau et al. (1990) *Plant Mol. Biol.* 15:127-136), bromoxynil (Stalker et al. (1988) *Science* 242:419-423), glyphosate (Shaw et al. (1986) *Science* 233:478-481) and phosphinothricin (De-Block et al. (1987) *EMBO J.* 6:2513-2518).

The expression systems of the present invention comprising a PdUBQ promoter of the invention operably linked to a gene of interest are useful for the transformation of a variety of plants. Preferably such plants include, but are not limited to, those which have economic value such as woody trees, such as *Eucalyptus* species (*E. alba, E. albens, E. amygdalina, E. aromaphloia, E. baileyana, E. balladoniensis, E. bicostata, E. botryoides, E. brachyandra, E. brassiana, E. brevistylis, E. brockwayi, E. camaldulensis, E. ceracea, E. cloeziana, E. coccifera, E. cordata, E. cornuta, E. corticosa, E. crebra, E. croajingolensis, E. curtisii, E. dalrympleana, E. deglupta, E. delegatensis, E. delicata, E. diversicolor, E. diversifolia, E. dives, E. dolichocarpa, E. dundasii, E. dunnii, E. elata, E. erythrocorys, E. erythrophloia, E. eudesmoides, E. falcata, E. gamophylla, E. glaucina, E. globulus, E. globulus* subsp. *bicostata, E. globulus* subsp. *globulus, E. gongylocarpa, E. grandis, E. grandis×urophylla, E. guilfoylei, E. gunnii, E. hallii, E. houseana, E. jacksonii, E. lansdowneana, E. latisinensis, E. leucophloia, E. leucoxylon, E. lockyeri, E. lucasii, E. maidenii, E. marginata, E. megacarpa, E. melliodora, E. michaeliana, E. microcorys, E. microtheca, E. muelleriana, E. nitens, E. nitida, E. obliqua, E. obtusiflora, E. occidentalis, E. optima, E. ovata, E. pachyphylla, E. pauciflora, E. pellita, E. perriniana, E. petiolaris, E. pilularis, E. piperita, E. platyphylla, E. polyanthemos, E. populnea, E. preissiana, E. pseudoglobulus, E. pukhella, E. radiata, E. radiata* subsp. *radiata, E. regnans, E. risdonii, E. robertsonii, E. rodwayi, E. rubida, E. rubiginosa, E. saligna, E. salmonophloia, E. scoparia, E. sieberi, E. spathulata, E. staeri, E. stoatei, E. tenuipes, E. tenuiramis, E. tereticornis, E. tetragona, E. tetrodonta, E. tindaliae, E. torquata, E. umbra, E. urophylla, E. vernicosa, E. viminalis, E. wandoo, E. wetarensis, E. willisii, E. willisii* subsp. *falciformis, E. willisii* subsp. *willisii, E. woodwardii*), *Populus* species (*P. alba, P. alba×P. grandidentata, P. alba×P. tremula, P. alba×P. tremula* var. *glandulosa, P. alba×P. tremuloides, P. balsamifera, P. balsamifera* subsp. *trichocarpa, P. balsamifera* subsp. *trichocarpa×P. deltoides, P. ciliata, P. deltoides, P. euphratica, P. euramericana, P. kitakamiensis, P. lasiocarpa, P. laurifolia, P. maximowiczii, P. maximowiczii×P. balsamifera* subsp. *trichocarpa, P. nigra, P. sieboldii×P. grandidentata, P. suaveolens, P. szechuanica, P. tomentosa, P. tremula, P. tremula× P. tremuloides, P. tremuloides, P. wilsonii, P. canadensis, P. yunnanensis*) and Conifers as, for example, loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*) and plantas such as cotton, coffee, cacao, tea, *Salix* species and *Citrus* spp.

The expression systems may be stably incorporated into plant genomes by, e.g., *Agrobacterium*-mediated transformation (Fraley et al. (1983) *Proc. Natl. Acad. Sci. USA.* 80:4803-4807) or by the biobalistics method (Klein et al. (1987) *Nature.* 327:70-73).

As used herein, the term plant or plant part includes reference to whole plants, plant organs (e.g., leaves, stems, roots, etc.) and plant cells and propagule of same.

As used herein, the term propagule includes a structure with the capacity to give rise to a new plant, e.g., a seed, a spore, or a part of the vegetative body capable of independent growth if detached from the parent.

All technical terms used herein are terms commonly used in biochemistry, molecular biology and agriculture, and can be understood by one of ordinary skill in the art to which this invention belongs. Those technical terms can be found in: Molecular Cloning: A Laboratory Manual, 3rd ed., vol. 1-3, ed. Sambrook and Russel, Cold Spring Harbor Laboratory Press, Cold Spring Harbor, N.Y., 2001; Current Protocols in Molecular Biology, ed. Ausubel et al., Greene Publishing Associates and Wiley-Interscience, New York, 1988 (with periodic updates); Short Protocols in Molecular Biology: A Compendium of Methods from Current Protocols in Molecular Biology, 5$^{th}$ ed., vol. 1-2, ed. Ausubel et al., John Wiley & Sons, Inc., 2002; Genome Analysis: A Laboratory Manual, vol. 1-2, ed. Green et al., Cold Spring Harbor Laboratory Press, Cold Spring Harbor, N.Y., 1997. Methods involving plant biology techniques are described herein and are described in detail in methodology treatises such as Methods in Plant Molecular Biology: A Laboratory Course Manual, ed. Maliga et al., Cold Spring Harbor Laboratory Press, Cold Spring Harbor, N.Y., 1995. Various techniques using PCR are described, e.g., in Innis et al., PCR Protocols: A Guide to Methods and Applications, Academic Press, San Diego, 1990 and in Dieffenbach and Dveksler, PCR Primer: A Laboratory Manual, 2$^{nd}$ ed., Cold Spring Harbor Laboratory Press, Cold Spring Harbor, N.Y., 2003. PCR-primer pairs can be derived from known sequences by using computer programs intended for that purpose (e.g., Primer, Version 0.5, 1991, Whitehead Institute for Biomedical Research, Cambridge, Mass.). Methods for chemical synthesis of nucleic acids are discussed, for example, in Beaucage and Caruthers (1981) Tetra. Lett. 22:1859-1862 and Matteucci and Caruthers (1981) J. Am. Chem. Soc. 103:3185.

The present invention is further illustrated by the following specific examples. The examples are provided for illustration only and are not to be construed as limiting the scope or content of the invention in any way.

Example 1

Expression Profile of Constitutively Expressed Polyubiquitin Genes

Expressed Sequence Tags (ESTs) from *Populus* sp. were clustered using the CAP3 program (Huang and Madan (1999) *Genome Res.* 9:868-877). Such ESTs were obtained from libraries representing the following tissues: apical shoot, bark, cambium, seed, xylem, leaf and root. The set of clusters thus generated was searched for those clusters composed of ESTs from all aforementioned libraries. Three clusters were chosen based on their high, homogeneous and constitutive level of expression in several tissues of *Populus*. These clusters represent gene sequences coding for isoforms of hexameric polyubiquitin. FIG. 1 shows the expression profile in several tissues of *Populus* for the three clusters representing the polyubiquitin genes whose promoters are disclosed herein. The series of histograms in FIG. 1 ultimately depicts the relative abundance of the polyubiquitin genes in cDNA libraries representing the aforementioned tissues (apical shoot, bark, cambium, seed, xylem, leaf and root). Thus, the histograms compose a set of digital expression data which is an approximation of the relative level of expression for the polyubiquitin genes whose promoters are disclosed herein.

Example 2

Isolation of PdUBQ Promoter Sequences

BLASTN was performed for the clusters referred to supra against the genomic sequences from *Populus trichocarpa* made available by the Joint Genome Institute, US Department of Energy, as part of the "*Populus* Genome Sequencing Project". Selected nucleotide regions from the clusters corresponding to putative exons were used as driver sequences in the retrieval of genomic sequence reads comprising the transcription initiation region and adjacent upstream promoter sequence for each of the three polyubiquitin genes represented by the three clusters referred to supra. These genomic reads were assembled using the PHRAP (Gordon et al. (1998) *Genome Res.* 8:195-202) program to obtain contigs encompassing 2700 nucleotides of putative promoter region upstream from the transcription initiation points of each of the three genes (+1 nucleotide, which corresponds to the beginning of the respective mRNA). These contigs contain the promoter regions for the polyubiquitin genes encoding the mRNAs represented by the three clusters concluded to be constitutively expressed in tissues of *Populus*.

For the physical isolation of the specific promoter regions, pairs of promoter-specific primers were designed based on the sequences of the promoter contigs described above to amplify by PCR a fragment of 2700 nucleotides from the promoter region of the polyubiquitin genes whose promoter sequences are disclosed herein. The first round of PCR was performed on genomic DNA from *Populus deltoides* or *P. trichocarpa*, which was prepared from leaves using the cetyltrimethyl-ammonium bromide (CTAB) extraction method (Aldrich and Cullis (1993) *Plant Mol. Biol. Report.* 11:128-141). The primers were designed to amplify the region upstream of the coding sequence, i.e., the 5' untranslated region, including the characteristic intronic sequence, and promoter region (PdUBQ) for each of the three polyubiquitin genes. The sequences of the primers used are given below for each promoter:

```
PdUBQ1:
                                       (SEQ ID NO: 4)
    5'- GAGAAAATGCTTCAAAAAGTCAGTATATAC -3'

(SEQ ID NO: 5)
    5'- TGCATCTGACACCCCAAAAAAGTAAAATCAG -3'

PdUBQ2:
                                       (SEQ ID NO: 6)
    5'- GGTCAAGTCGATCAATCGATTGATTCCTGT -3'

(SEQ ID NO: 7)
    5'- CATGCCTCCCCTCAAAAAAAGCACCAAGTG -3'

PdUBQ3:
                                       (SEQ ID NO: 8)
    5'- CCATGGGCACAGATGTGTTTGTCAAAGAAA -3'

(SEQ ID NO: 9)
    5'- CATCTGATCACATAACAAAACACGGACAAG -3'
```

Figure 2:
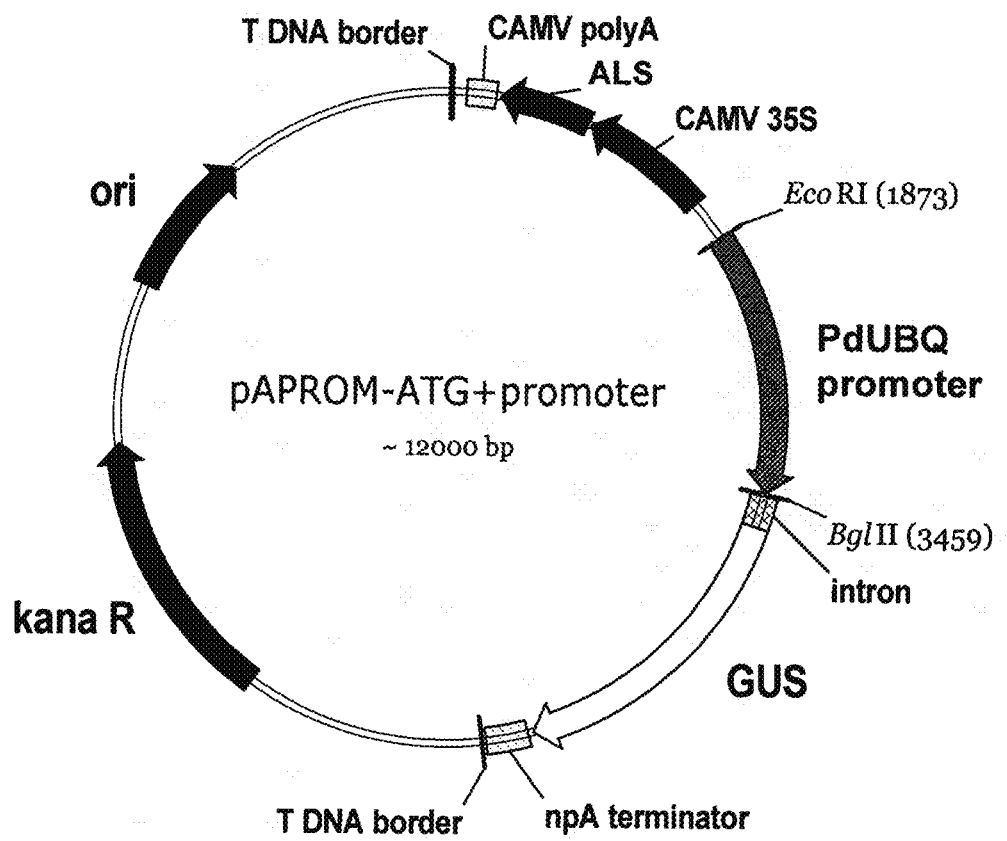
FIG. 2 schematically illustrates the plasmid vector pAPROM-ATG+promoter comprising the GUS reporter gene operably linked to a PdUBQ promoter sequence of the invention.
Figure 4:
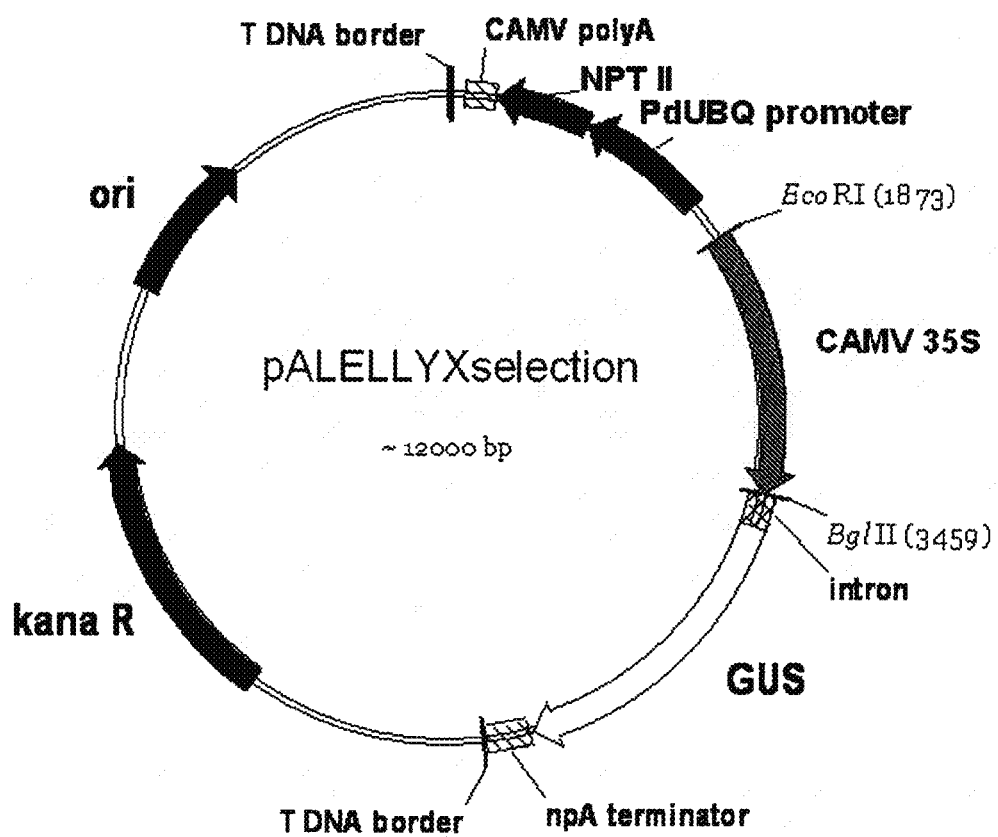
FIG. 4 schematically illustrates a plasmid vector comprising a selection gene driven by one of the PdUBQ promoters disclosed herein.

PCR was performed using commercially available reagents and cycle parameters of 5 min at 94° C. followed by 35 cycles of 94° C. for 1 min, then 55° C. for 1 min, then 72° C. for 3 min. Ten µl of the resulting amplified DNA fragments were run on a 0.8% agarose gel, purified using the GFX Gel Purification Kit (Amersham), subcloned into pGEM-T-Easy vector (Promega) and then into EcoRI and BglII sites of the pAPROM-ATG vector. Final sequences were determined on the resulting plasmids and set forth herein as SEQ ID NO.: 1, SEQ ID NO.: 2 and SEQ ID NO.: 3. FIG. 2 schematically illustrates the expression cassette pAPROM-ATG comprising the GUS gene operably linked to one of the PdUBQ promoters disclosed herein. FIG. 3 schematically illustrates the plasmid vector comprising a gene of interest operably linked to one of the PdUBQ promoters of the invention. FIG. 4 schematically illustrates the plasmid vector comprising the NPTII selection gene driven by one of the PdUBQ promoters disclosed herein.

Example 3

Transformation of Plants

Both dicot and monocot cells may be transformed or transfected with DNA constructs comprising or containing one or more of the PdUBQ promoters disclosed herein. Cells or plant organs, such as seeds, fruit, leaves, stems, wood, flowers and so forth, can be transformed or transfected. Exemplary of plants that can be transformed are those which have economic value such as, but not being limited to, tobacco, cotton, coffee, cacao, tea, *Salix* species, citrus spp, and woody trees, such as poplar, eucalyptus, pine, spruce, fir, etc.

Use of plant transformation methods in combination with the nucleic acid molecules of the invention or DNA constructs comprising the nucleic acid molecules of the invention results in transgenic plants or plant cells, as discussed supra. *Agrobacterium* such as *A. tumefaciens* or *A. rhizogenes* can be used, for example, in accordance with Nagel, et al. Microbiol. Lett 67: 325 (1990). In brief, the method is such that *Agrobacterium* may be transformed with a plant expression vector via, e.g., electroporation, after which the *Agrobacterium* is introduced to plant cells via, e.g., the well known leaf-disk method. Additional methods for accomplishing this include, but are not limited to, electroporation, particle gun bombardment, calcium phosphate precipitation, and polyethylene glycol fusion, transfer into germinating pollen grains, direct transformation (Lorz, et al., Mol. Genet. 199: 179-182 (1985)), and other methods known to the art. If a selection marker, such as kanamycin resistance, is employed, it makes it easier to determine which cells have been successfully transformed.

It is to be noted that the *Agrobacterium* transformation methods discussed supra are known as being useful for transforming dicots; however, de la Pena, et al., Nature 325: 274-276 (1987), Rhodes, et al., Science 240: 204-207 (1988), and Shimamato, et al., Nature 328: 274-276 (1989), all of which are incorporated by reference, have transformed cereal monocots using *Agrobacterium*. See also Bechtold, et al., C.R. Acad. Sci. Paris 316 (1994), showing the use of vacuum infiltration for introducing *Agrobacterium*.

Expression constructs can be prepared by cleaving one of the PdUBQ promoters obtained in Example 1 above with suitable restriction enzymes and inserting the fragment into the plant transformation vector pALELLYXgi together with an appropriate gene of interest (FIG. 3). The resulting expression construct is amplified in *E. coli*, and then transformed by tripartite conjugation (Nucleic Acid Research, 12, 8711 (1984)), freeze thawing, electroporation, chemical transformation or the like into *Agrobacterium tumefaciens* C58, LBA4404, EHA105 or the like.

Additionally, a promoter test expression vector can be prepared by ligating one of the promoters obtained in Example 1 to the GUS reporter gene (FIG. 2). The resulting expression vector, when transformed into plants, will direct the expression of GUS in the tissues where the promoter in question is active. Therefore, one may study the promoter activity and specificity by testing the transgenic plants using a chromogenic GUS assay such that cells and tissues where the PdUBQ promoter in question is active exhibit a blue color.

Transformation of citrus can be used for this purpose and is usually accomplished using co-cultivation of citrus epicotyl segments with *A. tumefaciens* (Annals of Botany 94, 67-74, (2004)).

To determine GUS activity, the explants were incubated in a substrate comprising 100 mM phosphate buffer (pH 7.0), 0.05% dimethyl suphoxide, 0.05% Triton X-100, 10 mM EDTA, 0.5 mM potassium ferrocyanide, and 1.5 mg/ml 5-bromo-4-chloro-3-indoly-β-D-glucuronide (X-gluc). The explants were subjected to 10 minutes of vacuum before overnight incubation at 37° C. After incubation, the number of blue spots was counted.

Figure 5:
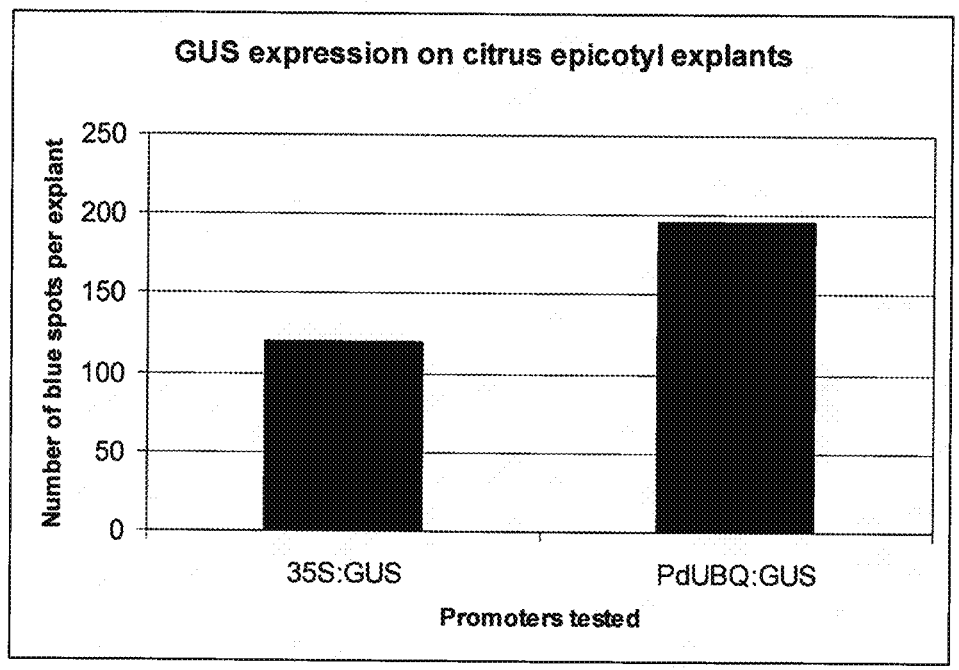
FIG. 5 shows the GUS expression in citrus epicotyl 3 weeks after transformation with an *Agrobacterium* carrying a plasmid vector comprising the GUS reporter gene operably linked to a PdUBQ promoter.

As shown in FIG. 5, explants transformed with the GUS reporter gene driven by a PdUBQ promoter presented a significantly higher number of blue spots (195 blue spots per explant) when compared to explants transformed with the GUS reporter gene driven by the CaMV 35S promoter (120 blue spots by explant).

Figure 6:
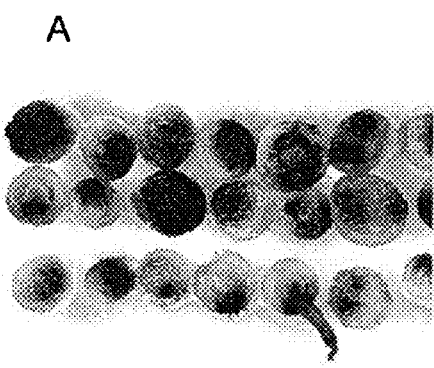
FIGS. 6A and 6B show the histochemical analysis of GUS activity in citrus epicotyl. A: tissues transformed with the plasmid vector comprising the GUS reporter gene operably linked to a PdUBQ promoter. B: tissues transformed with the plasmid vector comprising the GUS reporter gene operably linked to a CaMV 35S promoter.
Figure 6:
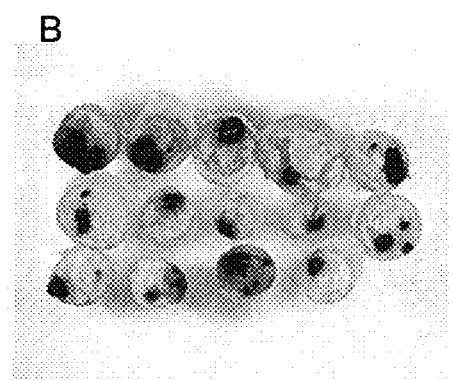

FIG. 6 presents the histochemical analyses of GUS activity in citrus explants. Citrus epicotyl segments transformed with a PdUBQ:GUS construct exhibited strong GUS expression in the whole explant (FIG. 6A), whereas explants transformed with the CaMV 35S:GUS construct showed only a weak staining (FIG. 6B).

Additionally, a promoter test vector can be prepared by ligating one of the promoters obtained in Example 1 to a selection gene (FIG. 4). The resulting vector, when transformed into plants, is expected to increase the expression of the selection gene in the tissues where the promoter in question is active, achieving much higher plant transformation frequencies.

Transformation of tobacco can be used for this purpose and is usually accomplished using the leaf disk method of Horsch et al. (Science 227, 1229, (1985)). The transformants are selected by growing on Murashige and Skoog medium containing 200 milligrams/liter of kanamycin. The transformed tobacco shoots are allowed to root on the medium, and are subsequently transferred to soil and grown, e.g., in a greenhouse.

Putative transformants were checked by NPTII ELISA assay, according to manufacturer's instructions (AGDIA PathoScreen kit for neomycin phosphotransferase II). ELISA demonstrated that from 60 regenerated tobacco plants, 57 (95%) presented high levels of NPTII protein when transformed with the PdUBQ:kanamycin construct (Table 1). From 59 regenerated plants, there were only 37 (62.7%) ELISA positive plants with the construct containing the NPTII gene driven by the CaMV 35S promoter.

These results indicate that the number of scapes (the regeneration of non-transformed plants) is much lower when a PdUDQ promoter drives the expression of the selection gene.

TABLE 1

Number of NPTII positive tobacco plants

| Construction | Number of Tested Plants | ELISA Tested Confirmed Positive Plants |
|---|---|---|
| PdUBQ:kanamycin | 60 | 57 (95%) |
| 35S:kanamycin | 59 | 37 (62.7%) |

Thus the data obtained with the citrus and tobacco transformation experiments show that this invention provides a promoter for use in transgenic plants that allows a higher level of expression of a gene product and also achieves higher selection efficiency.

What is claimed is:

1. An expression vector comprising:
   (a) an isolated nucleic acid molecule comprising a nucleotide sequence that initiates transcription of a nucleic acid molecule in a plant cell, wherein said isolated nucleic acid molecule comprises the nucleotide sequence set forth in SEQ ID NO:2 or 3, wherein said nucleotide sequence is capable of initiating transcription of a nucleic acid molecule in a plant cell, and
   (b) a heterologous nucleic acid molecule which encodes a protein of interest, wherein (a) and (b) are in operable linkage.

2. The expression vector of claim 1, wherein said expression vector is a plasmid.

3. A recombinant cell, wherein said recombinant cell is transformed or transfected with the expression vector of claim 1.

4. The recombinant cell of claim 3, wherein said expression vector is stably incorporated in said recombinant cell's genome.

5. A method of making a recombinant cell, wherein said method comprises transforming or transfecting a cell with the expression vector of claim 2.

6. A method of making a protein encoded by the expression vector of claim 2, comprising transforming or transfecting a cell with said expression vector to produce a recombinant cell, and culturing said cell under conditions favorable for the expression of said protein.

7. The method of claim 5, wherein said recombinant cell is a plant cell.

8. A method for making a protein, said method comprising culturing a plant or plant part which comprises the recombinant cell of claim 3, under conditions favoring production of said protein by said plant or plant part.

9. The method of claim 8, wherein said plant is a dicot.

10. The method of claim 9, wherein said plant is *Eucalyptus*.

11. The method of claim 9, wherein said plant is *Populus*.

12. The method of claim 8, wherein said plant is a monocot.

13. The method of claim 8, wherein said plant is a gymnosperm.

14. The method of claim 13, wherein said gymnosperm is *Pinus*.

15. The recombinant cell of claim 3, wherein said recombinant cell is a plant cell.

16. A plant or plant part comprising the recombinant cell of claim 15.

17. The plant of claim 16, wherein said plant is a dicot.

18. The plant of claim 17, wherein said plant is *Eucalyptus*.

19. The plant of claim 17, wherein said plant is *Populus*.

20. The plant of claim 16, wherein said plant is a monocot.

21. The plant of claim 16, wherein said plant is a gymnosperm.

22. The plant of claim 21, wherein said gymnosperm is *Pinus*.

23. The plant or part of claim 16, wherein said plant part is a propagule.

24. The recombinant cell of claim 3, wherein said recombinant cell is a pollen cell.

25. The method of claim 8, wherein said plant part is selected from the group consisting of a root, a stem, a leaf, a flower, a fruit, a seed, a pistil, a stigma, a style, an ovary, an ovule, an stamen, an anther, and a filament.

\* \* \* \* \*

SEQUENCE LISTING

<160> NUMBER OF SEQ ID NOS: 9

<210> SEQ ID NO 1
<211> LENGTH: 2703
<212> TYPE: DNA
<213> ORGANISM: Populus sp.

```
<400> SEQUENCE: 1
gagaaaatgc ttcaaaaagt cagtatatac ataacattct gtttgagata ttacatatac    60
aattctttaa gaacatcaac caccaatttg taatttatct ttaaattatt ttatacttac   120
tcttcaaaac taacaaactt agggttcctt actcttcatc tgtatgcaaa attcatctag   180
ttaaaccaaa catgttaaaa gatttaaaac aaattcctag tcatttaaat ctatcgcgca   240
cacgaggacc ccgtttattt actggaaagt agtttctttt tggaaagtga attccgggaa   300
agtgaattat ttttcgatgt ttggtagtgt aataggaaat aagttggaaa acatcttcca   360
gtgtttggtt atgtcatgga aaatgagctg gaaataact tattaatttt ttattttttt    420
tcaaatttat taaataatg aggaacaaat cttataaatt aaaagttga atgtgaatga    480 aattgaaaaa aaatataatt tcataaatta tctcaaataa aataataat aatcaaaata    540 atagagatca aatctaacaa ataaaaaaat taaaagatga agaaattaaa ataataataa   600
ttaccatttc ataaattatt tcaaataaaa taagtaacaa tcaaagaat gaggaccaaa    660 tttgatagat aaaaaatttc aattaaaaaa tgataaagga aaagcaaata acaattataa   720
aaatgaggac caaagttaat ataaaaatca aattctaagg gatgaaatta aaagaaatat   780
attcaaaaca atatatatat atatatatat atatatatat atatatatat atatatcaat   840
taaaaatttg aggaccaaat ttgatataat caacaaataa tatgatattt ttaaaatttt   900
cacaactttc gaaaaatatt tttcgcttaa aataaaagga aaacactttc ctagaaacca   960
agtcgaattt ttctttaact aaaaaatgtt ttccgtcgat cagctaaaca cagaaaagtt  1020
tgaaaaataa ttttcaaaaa aacattttt tgtcaaacat acaatgtcta ggtttgcaaa  1080
tattgaaaaa agtcaaatct cacgtcttta agcttttttt tttaatataa aaaaattatt  1140 atttttatg attttataat ttttttttgt tttttatttt ttttcatcat aaatggatgg   1200
tgacggagtt gtccaccaaa tccagacccc ttttgcaagt tgtgtgatcc atattatagg  1260
cgtaagcaga cggctaccca ccgtttactc gttcctttcc cttccaactc cgcaacactc  1320
caaataagaa agatatcaac taatcattca aggtgcgtgg actacactgc ctcaattact  1380
taattttggt tttttatatg cacacacttt taacgtggaa aatattctat tttggctttc  1440
tttttatatt tttattttgt attttttattt atttattat ataaagata tttaaaataa   1500 ccttgctaac ttgtgtttaa attaaattat tctatctaaa tatttaaatc aaacctcaaa  1560
attatacaaa ttaatatata tttgtaattt tatttagttt gatgactgga aatcaactag  1620
taataagctt gtagaaagaa aaaaatttaa atttaacagt agataaaaac aaaataagat  1680
tctagccgta ataattttt taaataaaaa attattttca aattaaaaat taactcatta  1740 tttttttcata gcaatataac gacgtaaatc caacagaaaa ttttttttttt tttccttaca  1800 aacaaacagg aaaattcaaa tacggaaata ccgcataaca cacgcgtact cgaagagcgt  1860
agtccttttc tctcactctc agtttcctag caatatccgc ccccactaga cgccactgat  1920
aaaaggaaaa acaaccaaga agtcttccgg aaggatcatc ctaagacgtg gcgtttcata  1980
attagacgct gcaaccgggt attcccgtaa tttcaccatc aaatttctat gatatattga  2040
gacgctccag ctctcttctc ctcacagttg tgattattc ttctctatca aaatctttaa   2100
acagctctca ttcaaggtat gcctctcgtg tccgattgtc tagttttttc ttaaatttat  2160
ttttaaataa ataattgtta tacgatctgt tagtgtttta tggatcagtc cttaataatc  2220
gtttattgat gacagtaatc tgttttttttt tttatctgga tattacgacg ttgttattga  2280
ttctattgtt tagatctcga ttgatggggg taatcgagga ccctttccat tttttttttca  2340
```

```
aattttgatc aattgattta ttctgttaag atctgttagt gctttacgga taacatagat    2400
ctgcctgatg ttcagattta tttatctcga tcttagggct ctattattaa ctctgtttag    2460
atctcgattg gtcggtgttt tcaagggcct cttaagattt gattaattaa ttaattaatt    2520
aatatggatc atgtttctat tcgtttaatt ttgatgctat tttgattaaa agaaaaggtt    2580
atcgtttttt tttttaaatg atcaattgaa tttgtttgct attgttaatg atctgaagga    2640
ttgttatatg ttgagatctg aatctagttt gtctctgatt ttactttttt ggggtgtcag    2700
atg                                                                 2703
```

<210> SEQ ID NO 2
<211> LENGTH: 2703
<212> TYPE: DNA
<213> ORGANISM: Populus sp.

<400> SEQUENCE: 2

```
ggtcaagtcg atcaatcgat tgattcctgt agaattatca ggtgttcata acaaataaac      60
aaatggtcga ccgattcatt cgattaagct aaatgatcga tcggttcata cagaattcca     120
tattcattaa ttttaattaa cctaggtgaa ttcttagaat cgtctatcaa gttttttatca     180 atctttttata tgtatgttta gtgtgcattc attttaattt gtgctatcaa gatgagatat     240
acatatttat atataaacac taaaatgaac atttagttct aagtctttaa tatgcttcat     300
tcttggactt cttcttgatt tcttcatgaa atcctctatg cttatttata taatgtttat     360
ataaacctgt ttaaaattta ttcttaacca actatattat tagtccaaat ttcttattat     420
ttttatcatc aaaatacata taaaaacata aatgtgttat ctaaaggtca atacttgtaa     480
agattttaaa taattttcag tagcaagaag gtgatttcaa gttgcaacca gcaaaacttc     540
aaaactacaa ttaagtcaat gaaatatgag aaatgcaata gccttgcgta tagactttgc     600
cttacatgaa atcaatcaat gttgaagaag gtgatagttt catggaattt gggcatcggg     660
tagattagtc taaatggcct tgtaatgagc atttaatgca tttgctgttt tttctttctt     720
ttttttctta acttagaaaa ttttcatgaa gaaaatggta aaatattgca tgtgaaagca     780
tacagaaaaa aaatgaagct tcaaagaact atttggagaa atttcaccta ttttttctctt     840 tgtgtaatca atgtaatcgt tgtgggcata tggtagggat ataattacat ttctcagaaa     900
gaataaggac gatcttaaaa cttggtattg cgtccccgca ttatcttctt acaattattt     960 tatttgttttt tttagctttt tatcaacaag tccactacac cctaacaccg tttgcaactt    1020
gtgatctatt ctattggcga aagcaacggc tacctaccgt ttactcattc caacacggca    1080
agacgccgga aaagaaagat ctaaactaat aatcgttcat actgcgtgca cgacactccc    1140
tcaattattt aattccttgtt ttttttcata gttttttaaat tcagcccggt aattaacccg    1200
gtttaatatc tgagtttcaa gttttgaccg ggttaattct gattttttga aaaaattaaa    1260
acatcatcgt tttaataaaa aataaaagtc aatgggttac aactgaattt ttgatcgagt    1320
tttgctgggt ccaccgggtc aaccctccgg gtcagccggg tcaccctgac attgacttcc    1380
tctatatttt ataaaacccg gcgttgtttc agccctggt tgacccagaa aaaccatgc    1440 tttatattaa aaaatataa acaaatagta agtttctttc acataaaatt ttagataaat    1500
agtttgtact taataaaaaa tattatgaaa gtattgttttt tcatatttga ttaaaactca    1560
gaattatata aaaaaataat tttttttgtt ttttaattc aagtgtttaa tttaataatt    1620
gtaaatcaag taataaactg gtaagaaaaa tagaaaatca gaataaaatg gagagctaaa    1680
```

-continued

```
tagaaaatgt gagcaaaaaa aatagataaa tgcaggagtt cttacttcaa taacttgtcg    1740
gatacagaag gaattgattt tagcaatgaa taaattggcc ataaaataat ttgtttttaa    1800
aaaagttcat tacttgtgat tctccacttt acatatatga tagtagcgcg taagcacgcg    1860
tgctggaaga gcgtggtact ttcacctcgg cttccttaac aatatccggc tccactagaa    1920
ccacctagaa atgagaattg atgaaaaaaa ggaaaaacat aaacctgagt cttcggcaaa    1980
aattatccaa atacgtggcg tgtttcaatt gggtattctg atagggcatt ccggtaattt    2040
catcaccgag tttctactat atatgaagac ggtctgctag ccttcttcac ctcacatttg    2100
tgataatatc tttcttccct aacaaagcat tcaactcttt caaggtatgc ctcttcgtct    2160
ccatttcttg ttttttcatat gtttgtgtgt ctatatatgt atatatatta atttattgat   2220
gcttaattct taagatctgt tagttttttta tggattaatc ctgaaaagtt gattgattaa    2280
taactagaga tctgtttgat gttttgatgt tttattgatt ttgttgttca gatcttgatt    2340
ggtcctcgtt tgctagggcc ttataagatt tgattaatta atataaatca tgttttttt     2400 cgtttaattt tgatgttaat ttgtttaaag gaaaggaatt ttcttatgat ttttcagct     2460 ttgatccatt gacttttaat ttcttagctt attttagat gatttgtaga tataatattg     2520
taaaatcttt ttttttatac taccgatcag gcaaaatttt ttttttttca tattgaattg    2580
gttggttgaa actttttca tatattttgt tgaatttctg tctgatttgt gggttacaaa     2640
cataaatcat acgatgtatc tgatctggtt tttcacttgg tgctttttt gaggggaggc     2700 atg                                                                 2703
```

<210> SEQ ID NO 3
<211> LENGTH: 2703
<212> TYPE: DNA
<213> ORGANISM: Populus sp.

<400> SEQUENCE: 3

```
ccatgggcac agatgtgttt gtcaaagaaa atgaatggaa atcttatcct ttgctggtga     60
gttttttcct tcgccttcac ctattccctt acaattcctt tcttctctta tatttctttt    120
gcgtgctgca caactttggt gctatcaagt gaaattcaca gtgtcttgca ttctattttc    180
aatgcaggcc taaggtact cttgcaagca acatacagtc tcagaggcaa gatgttttgt     240
tttgtgtttg caattggaaa tagccttctt gttataacta tttgttacat ctttacatca    300
atttgaactc tctgttgcta tgaatggcag atgatgaaaa gtatggcatt atttctttct    360
attgtttact gcaatagtca ctgacatagg aggaatgtta ttaaaccggc tgggctggct    420
ataaatcggt ccaagatcca agttacgagt tgagcgaatt gacccaaata atcgtgtatg    480
gacaacacta aagcaaaggc ataagacagc atgtcaggca tagttcctat gacgagttta    540
ttaaaaatgt tcaaaagaa tttgggactg caagaacaag gtcaatttgc acaagtcttc     600
aaaagatttg gattaaccca agttaattta ccgtatttgt aacctaatcc ttgaccgagc    660
cggttcaaga atcaaatcat ataaccatcg cccacagaac cttcccggga agaaaaaaac    720
gttgagagtt tccttggact ttctttgac gggtcaagct tggcagatgg aagtaaaaga     780
cgttgggagc ccttccccat gaaaagaaga gtcgttctta gctttctct gaagggtcaa     840 gcttggagga tgggataaca attattctag acccaaaaag aaaaactcct tgcttgaaaa    900
ccacaagaat ttagttctaa ttctgtgcaa tgctacccct gaaaaataat tatattgatg    960
gttttaatgt gttgatataa aaaattaaaa atatttaat aaattttaa ataaaaaata     1020 aattaaacta cagtattaaa cacaagctaa ataattaaaa aaaaaattca ctaatcgatg    1080
```

-continued

| | |
|---|---|
| ataattctgt gcaatgacca ggaagatgat tgtcttgccc atgatatatc cttctccatg | 1140 |
| tcacctgtga tgctacaaat cactgatcaa taactcggtt gcgtaataat aagagcttgg | 1200 |
| aattaaaaga tttgtttttt ctgtgatctc aggttcgagt tatgtagttg ctagtatgat | 1260 |
| ggtcactgaa agcttctata gtcattaact tcagagctcg tgggattagt tgaggtactc | 1320 |
| gcaggttagc ctgaacaccc acattcaaaa aaaaaaaact tggttgctca acaacaaaag | 1380 |
| tttacaataa aatactaaaa acttgagaga ttattaggta attttttta attagatacc | 1440 |
| cggaataact tgtttatatc tcaactaatt tcacgaattt taaagtaaat aataatataa | 1500 |
| accttcagta accctgagat tgtgggact cgaactaatt attttagaa aataaactca | 1560 |
| aaacctgacc aattaagcta tacccttcaa aattagctaa tttaatttgc tatatcattg | 1620 |
| gatgaaaaaa tatataaaaa acattaataa aactttatga aatgcttaca ctataaaccg | 1680 |
| agatattata ttttatctac gtgttatgtg tttattggtg taatttatag tataattatt | 1740 |
| aaactccatt aaattaaggt aacccatcga tgctcatgac aggtcagaca actgtgatgt | 1800 |
| ataggtgata tcgtaaaact acttctacct aaccatttgt tttaagaaaa aaattatgaa | 1860 |
| aaagggaaaa aagaaaatat ctaccggcat tgtagtgtcg gtccaataag aggagcgcgt | 1920 |
| gtgaataatc aagccagaga agcgtgactc attccttctt tgtctccagg tcattatcgt | 1980 |
| caattcgcta tataatttct agtataaatc aataacctgg agccccaatt ctctcacaat | 2040 |
| ttcaatcaaa acaatcccta aaattctctc aaatctctat ctctcaaggt atgatctgat | 2100 |
| cctcaattc tgtttaatac tctttgtaca atccttaatc gattcattat ttcgtgatct | 2160 |
| gtttgttgat tgatgttatc gatttcatga gttttttttt tggatctcta aatttagtga | 2220 |
| gattaaagga tctgtctttg tttcggctaa gcgtatagat tttgttactt taggtattta | 2280 |
| ttcttctttt attgaaaaaa tatgatcttt tatgattat tagttatcgg ttttttcttct | 2340 |
| ctgtttttac aatcattatt ttttatttat ttcttttatt gattaaaaag ttgtgatctt | 2400 |
| tgagggttac ttaattgatt tgtgaaaggt tttgttaaga gtcctaaaat aatcagtatt | 2460 |
| ttgaaaattc taaatatttt ttttaggatt gatcgatatg tgtttcatct gcttgattga | 2520 |
| cttgatcttc tgattgatta tatctgtgca agattttgaa aatatgcttg atgggtcttt | 2580 |
| ttattttgtg atgagattat gagattgatc gataagtgat gcatttgtgg ggtgtgatga | 2640 |
| agaagatttt tcctattttt gaaattggct gatcttgtcc gtgttttgtt atgtgatcag | 2700 |
| atg | 2703 |

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gagaaaatgc ttcaaaaagt cagtatatac                                30

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 5
tgcatctgac accccaaaaa agtaaaatca g                              31

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtcaagtcg atcaatcgat tgattcctgt                                30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catgcctccc ctcaaaaaaa gcaccaagtg                                30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccatgggcac agatgtgttt gtcaaagaaa                                30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
catctgatca cataacaaaa cacggacaag                                30
```